(12) United States Patent
Thaper et al.

(10) Patent No.: US 8,278,461 B2
(45) Date of Patent: Oct. 2, 2012

(54) STABLE AMORPHOUS FORM OF CARVEDILOL DIHYDROGEN PHOSPHATE WITH STABILIZER

(75) Inventors: Rajesh Kumar Thaper, Pune (IN); Manoj Devilalji Prabhavat, Pune (IN); Yogesh Dadaji Pawar, Pune (IN); Pritesh R. Upadhyay, Pune (IN)

(73) Assignee: Lupin Limited, Mumbai, Maharashtra (IN)

( * ) Notice: Subject to any disclaimer, the term of this patent is extended or adjusted under 35 U.S.C. 154(b) by 30 days.

(21) Appl. No.: 12/674,642

(22) PCT Filed: Aug. 6, 2008

(86) PCT No.: PCT/IN2008/000486
§ 371 (c)(1),
(2), (4) Date: Feb. 10, 2011

(87) PCT Pub. No.: WO2009/024997
PCT Pub. Date: Feb. 26, 2009

(65) Prior Publication Data
US 2011/0124879 A1 May 26, 2011

(30) Foreign Application Priority Data

Aug. 21, 2007 (IN) .......................... 1152/KOL/2007

(51) Int. Cl.
*C07D 209/82* (2006.01)
(52) U.S. Cl. ..................................... 548/444
(58) Field of Classification Search .................. 548/427, 548/444
See application file for complete search history.

(56) References Cited

U.S. PATENT DOCUMENTS

| | | | |
|---|---|---|---|
| 4,503,067 A | 3/1985 | Wiedemann et al. | |
| 6,515,010 B1 | 2/2003 | Franchini et al. | |
| 7,056,942 B2 | 6/2006 | Hildesheim et al. | |
| 7,268,156 B2 * | 9/2007 | Brook et al. | 514/411 |
| 7,777,053 B2 * | 8/2010 | Sanganbhatla et al. | 548/444 |
| 7,893,100 B2 * | 2/2011 | Brook et al. | 514/411 |
| 8,114,900 B2 * | 2/2012 | Ini et al. | 514/411 |
| 2005/0148779 A1 | 7/2005 | Chen et al. | |
| 2005/0240027 A1 | 10/2005 | Brook et al. | |
| 2005/0261355 A1 | 11/2005 | Chen et al. | |
| 2005/0277689 A1 | 12/2005 | Brook et al. | |

FOREIGN PATENT DOCUMENTS

| | | |
|---|---|---|
| IN | 119/KOL/2007 | 1/2007 |
| WO | WO 2004/002419 A2 | 1/2004 |
| WO | WO 2008/002683 A2 | 1/2008 |
| WO | WO 2008/070072 A2 | 6/2008 |
| WO | WO 2008/083130 A2 | 7/2008 |
| WO | WO 2008/084494 A1 | 7/2008 |
| WO | WO 2008/093350 A1 | 8/2008 |
| WO | WO 2008/104990 A1 | 9/2008 |

OTHER PUBLICATIONS

Pokharkar et al., "Development, characterization and stabilization of amorphous form of a low $T_g$ drug," *Powder Technology* (2006) 167: 20-25.
Hancock et al., "Molecular mobility of amorphous pharmaceutical solids below their glass transition temperatures," *Pharmaceutical Research* (1995) 12(6): 799-805.
Chiou et al., "Pharmaceutical applications of solid dispersion systems," *Journal of Pharmaceutical Sciences* (1971) 60 (9): 1281-1302.
Yokoi et al., "Changes in surface properties by granulation and physiochemical stability of granulated amorphous cefditoren pivoxil with additives," *International Journal of Pharmaceutics* (2004) 280: 67-75.
Yoshioka et al., "Inihibition of indomethacin crystallization in poly(vinylpyrrolidone) coprecipitates," *Journal of Pharmaceutical Sciences* (1995) 84 (8): 983-986.
Yamashita et al., "Establishment of new preparation method for solid dispersion formulation of tacrolimus," *International Journal of Pharmaceutics* (2003) 267: 79-91.
Marsac et al., "Theoretical and practical approaches for prediction of drug-polymer miscibility and solubility," *Pharamaceutical Research* (2006) 23 (10): 2417-2426.

* cited by examiner

*Primary Examiner* — Golam M M Shameem
(74) *Attorney, Agent, or Firm* — Merchant & Gould P.C.

(57) ABSTRACT

The present invention provides a novel stable amorphous form of carvedilol dihydrogen phosphate and the process for its preparation that involves reaction of carvedilol base with ortho phosphoric acid in the presence of stabilizer in a suitable solvent or mixture of solvents followed by concentration and isolation. An alternate process for preparation of amorphous form of carvedilol dihydrogen phosphate involves addition of stabiliser to the solution of stable amorphous or crystalline carvedilol dihydrogen phosphate in a suitable solvent or mixture of solvents followed by concentration and isolation. The novel stable amorphous form of carvedilol dihydrogen phosphate is highly stable.

13 Claims, 10 Drawing Sheets

STABLE AMORPHOUS FORM OF CARVEDILOL DIHYDROGEN PHOSPHATE WITH STABILIZER

This application is a National Stage Application of PCT/IN2008/00486, filed Aug. 6, 2008, which claims benefit of Ser. No. 1152/KOL/2007, filed Aug. 21, 2007 in India and which applications are incorporated herein by reference. To the extent appropriate, a claim of priority is made to each of the above disclosed applications.

FIELD OF THE INVENTION

The present invention relates to a novel stable amorphous form of carvedilol dihydrogen phosphate that is highly stable and process for its preparation.

BACKGROUND OF THE INVENTION

Carvedilol has structure as shown in formula 1. Carvedilol is disclosed in U.S. Pat. No. 4,503,067 (assigned to Boehringer Mannheim, GmbH, Germany) and it is chemically known as (±)-1-(9H-carbazol-4-yloxy)-3-[[2(2-methoxyphenoxy)ethyl]amino]-2-propanol.

I

Carvedilol is a racemic mixture of R(+) and S(−) enantiomers. Both enantiomers are nonselective β-adrenergic blocking agent with $\alpha_1$ blocking activity while S(−) enantiomer also has non-selective β-adrenoreceptor blocking activity. Carvedilol is used for treatment of hypertension, congestive heart failure and angina.

There are several patents and patent applications that are directed to crystalline salts and solvates thereof and also to their preparation.

The product U.S. Pat. No. 4,503,067 (Boehringer Mannheim) describes salts of carvedilol with acids such as hydrochloric acid, hydrobromic acid, phosphoric acid, sulphuric acid, acetic acid, citric acid, maleic acid or benzoic acid.

The U.S. Pat. No. 6,515,010 covers carvedilol methane sulfonate.

Another U.S. Pat. No. 7,056,942 assigned to Teva discloses crystalline carvedilol hydrochloride hydrate.

The patent application US 2005/240,027 (assigned to SmithKline Beecham) disclose crystalline carvedilol dihydrogen phosphate hemihydrate, carvedilol dihydrogen phosphate dihydrate, carvedilol dihydrogen phosphate, carvedilol dihydrogen phosphate methanol solvate and carvedilol hydrogen phosphate.

In the patent application US 2005/277,689 (assigned to GlaxoSmithKline) crystalline salt, forms or solvate of carvedilol selected from the group consisting of carvedilol mandelate, lactate, maleate, sulfate, glutarate, mesylate, phosphate, citrate, hydrogen bromide, oxalate, hydrochloride, benzoate and corresponding forms or solvates thereof are described.

The patent application US 2005/261,355 (assigned to SB Pharmco) covers carvedilol hydrobromide monohydrate and carvedilol hydrobromide.

The patent application US 2005/148,779 (GlaxoSmithKline) claims crystalline carvedilol monocitrate monohydrate We have filed an Indian patent application 292/KOL/2007 dated 27 Feb. 2007 in Indian Patent Office on amorphous form of carvedilol dihydrogen phosphate and the process for its preparation. The amorphous form obtained by the process described in this application has glass transition temperature below 60° C. The amorphous solids in general having low glass transition temperature not only create complications during formulation but also has stability related problems on storage. The glass transition temperature is the temperature, below which the physical properties of amorphous materials vary in a manner similar to those of a crystalline phase (glassy state), and above which amorphous materials behave like liquids (rubbery state). A materials glass transition temperature is the temperature below which molecules have little relative mobility. Thus, there exist a need to develop stable amorphous form of carvedilol dihydrogen phosphate which have improved characteristics.

The synthetic exploration of novel crystalline forms, amorphous form and/or solvates thereof of a pharmaceutically active compound provides a possibility to a organic chemist, to obtain a new form or solvate that has improved characteristics such as bulk density, particle size, stability, solubility in aqueous solution and ease of processing in the formulation for preparing suitable pharmaceutical dosages.

In case of carvedilol dihydrogen phosphate, the patent as well publication literature lack in providing information on stable amorphous form of carvedilol dihydrogen phosphate, thereby indicating poor attention given by the synthetic chemists for its isolation and preparation. The present invention is directed to the stable amorphous form of carvedilol dihydrogen phosphate and to also to the development of process for its preparation.

SUMMARY OF THE INVENTION

The present invention provides a stable amorphous form of carvedilol dihydrogen phosphate and process for its preparation. The process for the preparation of stable amorphous form of carvedilol dihydrogen phosphate comprises of:
(a) preparation of a solution of carvedilol base in a suitable solvent or mixture of solvents,
(b) addition of stabiliser,
(c) addition of ortho phosphoric acid,
(d) removal of solvent, and
(e) isolation of solid.

Another process for the preparation of stable amorphous form of carvedilol dihydrogen phosphate comprises of:
(a) preparation of a solution of polymorph hydrate of carvedilol dihydrogen phosphate in a suitable solvent or mixture of solvents,
(b) addition of stabiliser,
(c) removal of solvent, and
(d) isolation of solid.

Accordingly, the present invention provides a thermodynamically stable amorphous form of carvedilol dihydrogen phosphate having glass transition temperature in the range between 50° C.-176° C.

DETAILED DESCRIPTION OF THE INVENTION

The inventors of the present patent application have surprisingly and unexpectedly found that a novel stable amorphous form of carvedilol dihydrogen phosphate can be prepared which is highly stable.

Accordingly, the present invention provides a thermodynamically stable novel form of carvedilol dihydrogen phosphate that is highly stable.

Figure 1:
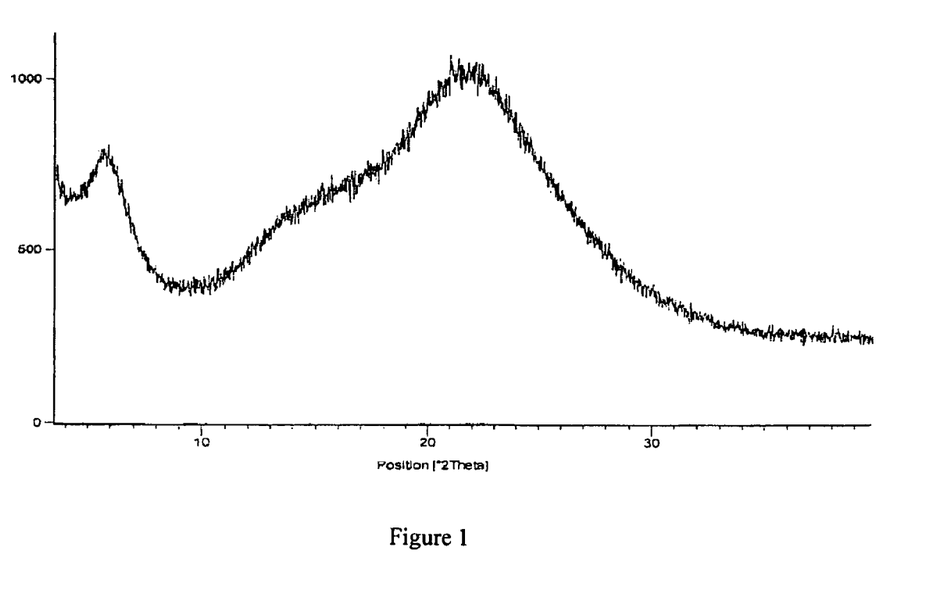
FIG. 1: PXRD of stable amorphous form of carvedilol dihydrogen phosphate obtained by using 5% PVPK-30 as stabiliser.
Figure 2:
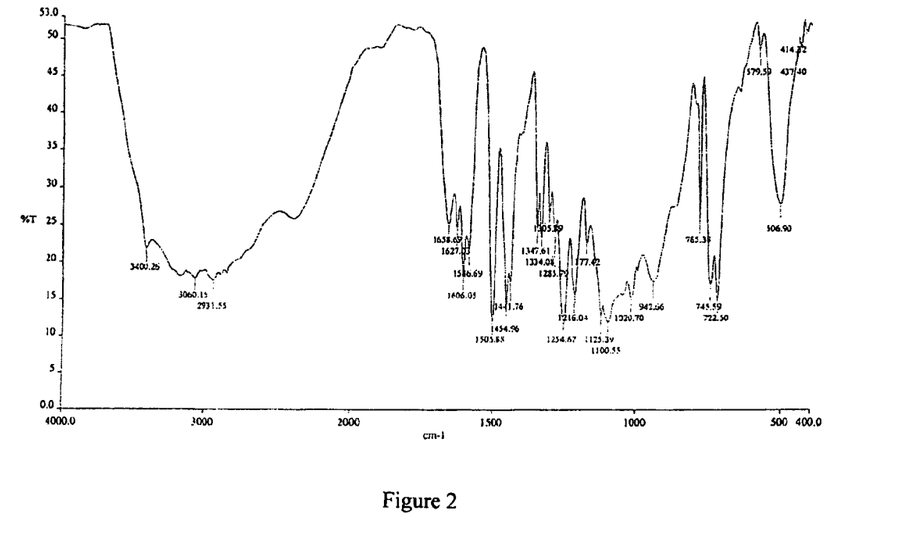
FIG. 2: FT-IR spectrum of stable amorphous form of carvedilol dihydrogen phosphate obtained by using 5% PVPK-30 as stabiliser.
Figure 3:
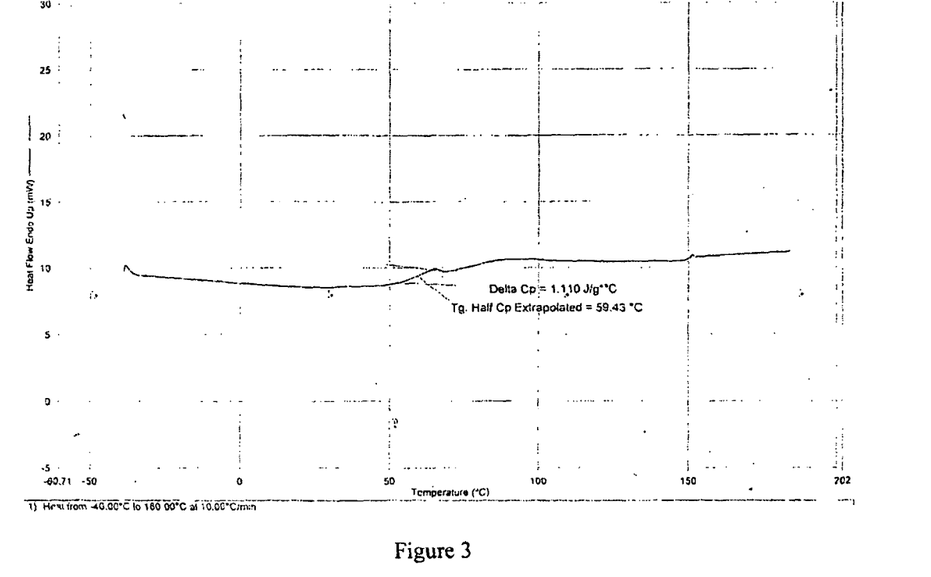
FIG. 3: Differential Scanning calorimetry (DSC) of stable amorphous form of carvedilol dihydrogen phosphate obtained by using 5% PVPK-30 as stabiliser.
Figure 4:
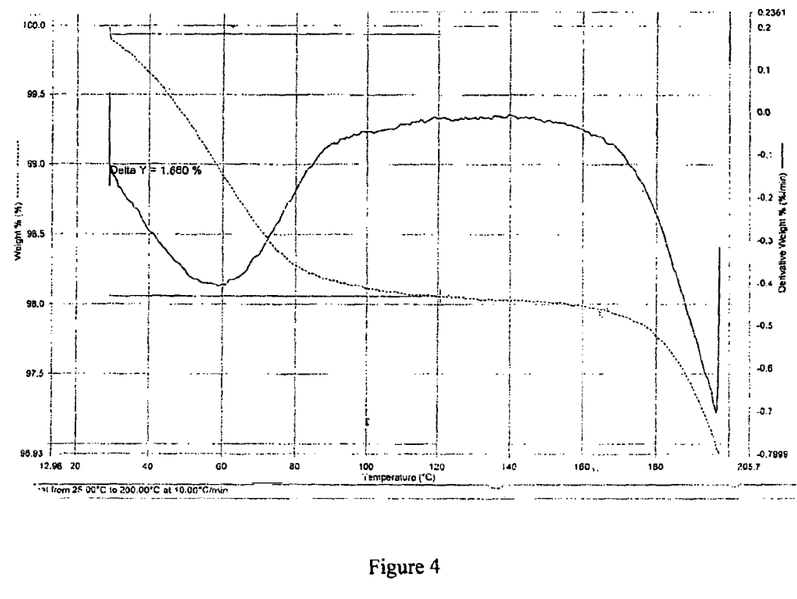
FIG. 4: Thermal Gravimetric Analysis (TGA) of stable amorphous form of carvedilol dihydrogen phosphate obtained by using 5% PVPK-30 as stabiliser.

The novel stable amorphous form of carvedilol dihydrogen phosphate of the present invention is characterized by X-ray diffractogram as shown in FIG. 1, FT-IR spectrum as shown in FIG. 2, DSC as shown in FIG. 3 and TGA as shown in FIG. 4. The amorphous carvedilol obtained without stabiliser having glass transition temperature 55-56° C. while the stable amorphous form of the present invention has glass transition temperature in the range between 76 to 185° C. The phosphorous content of the stable amorphous form of the present invention is between 18-20% on anhydrous basis.

Figure 6:
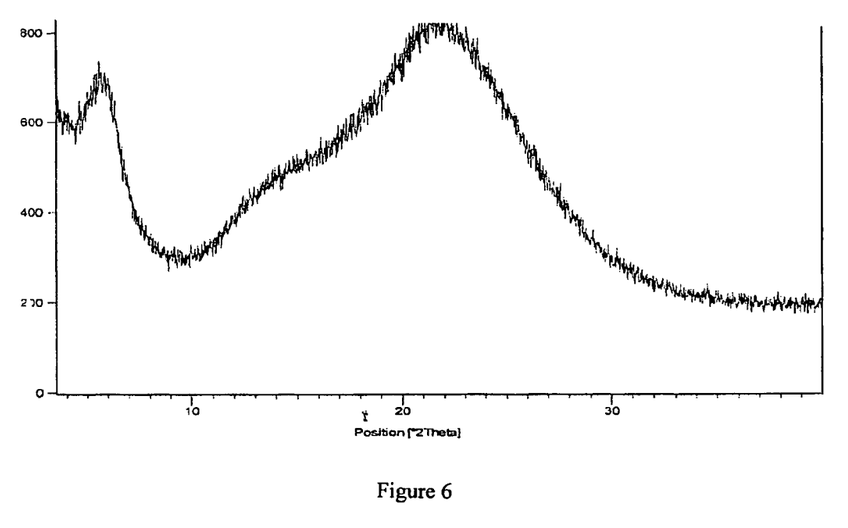
FIG. 6: PXRD of amorphous form of carvedilol dihydrogen phosphate without stabiliser.
Figure 7:
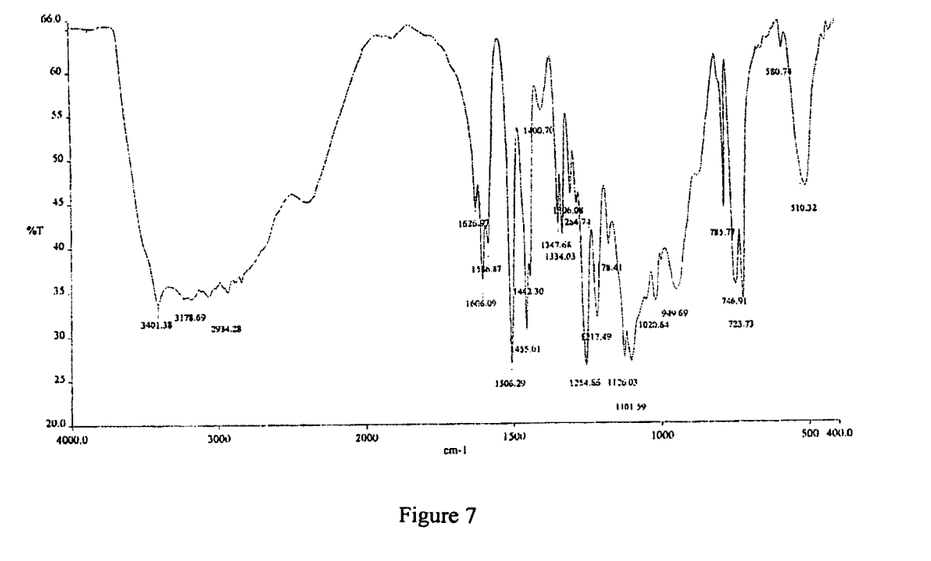
FIG. 7: FT-IR spectrum of amorphous form of carvedilol dihydrogen phosphate without stabiliser.
Figure 8:
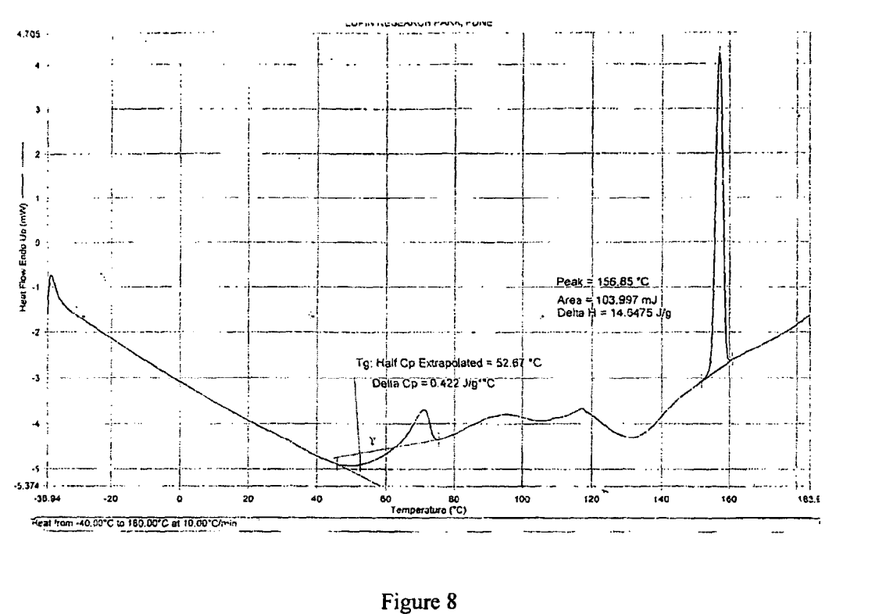
FIG. 8: Differential Scanning calorimetry (DSC) of stable amorphous form of carvedilol dihydrogen phosphate obtained by using 5% PVPK-30 as stabiliser.
Figure 9:
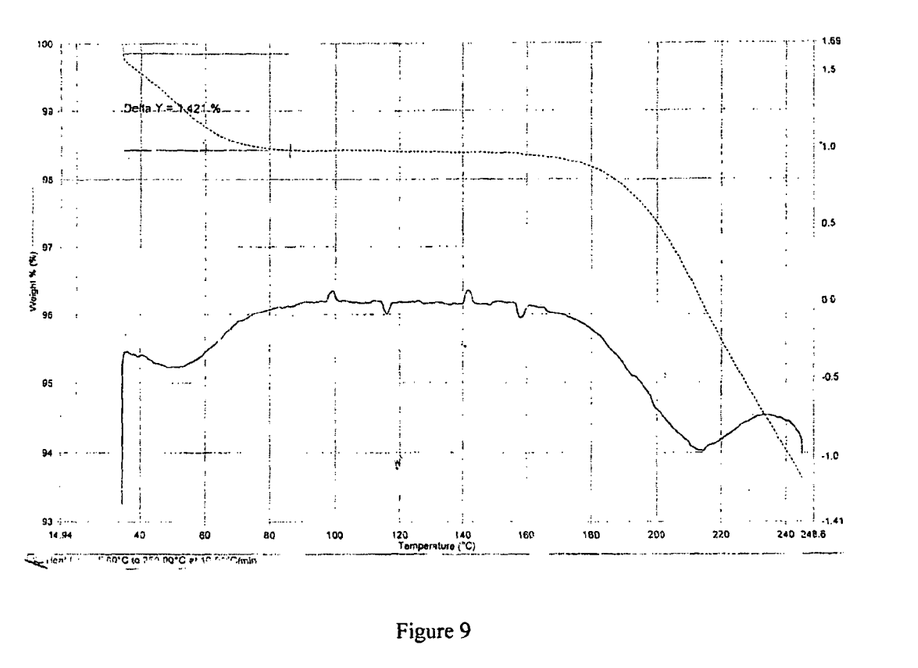
FIG. 9: TGA of amorphous form of carvedilol dihydrogen phosphate obtained without stabiliser.

The amorphous form of carvedilol dihydrogen phosphate without stabiliser was prepared according to the method described in application 119/KOL/2007 dated 31 Jan. 2007 files in Indian Patent Office which are described in examples 8 and 9 in the experimental section. The amorphous form of carvedilol dihydrogen phosphate obtained without stabiliser is characterized by X-ray diffractogram as shown in FIG. 6, FT-IR spectrum as shown in FIG. 7, DSC as shown in FIG. 8 and TGA as shown in FIG. 9.

Figure 10:
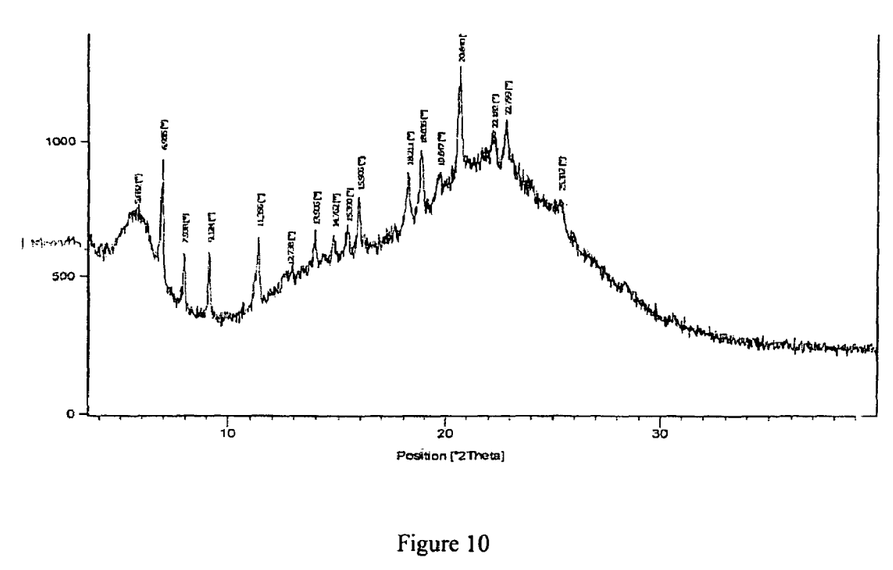
FIG. 10: PXRD of amorphous form of carvedilol dihydrogen phosphate without stabiliser after 1 month at 40° C.±2° C. (RH 75%).

The PXRD of amorphous form of carvedilol dihydrogen phosphate without stabiliser after 1 month at 40° C.±2° C. (RH 75%) is shown in FIG. 10. It shows appearance of several sharp peaks indicating slow conversion of amorphous form in to crystalline form.

Figure 5:
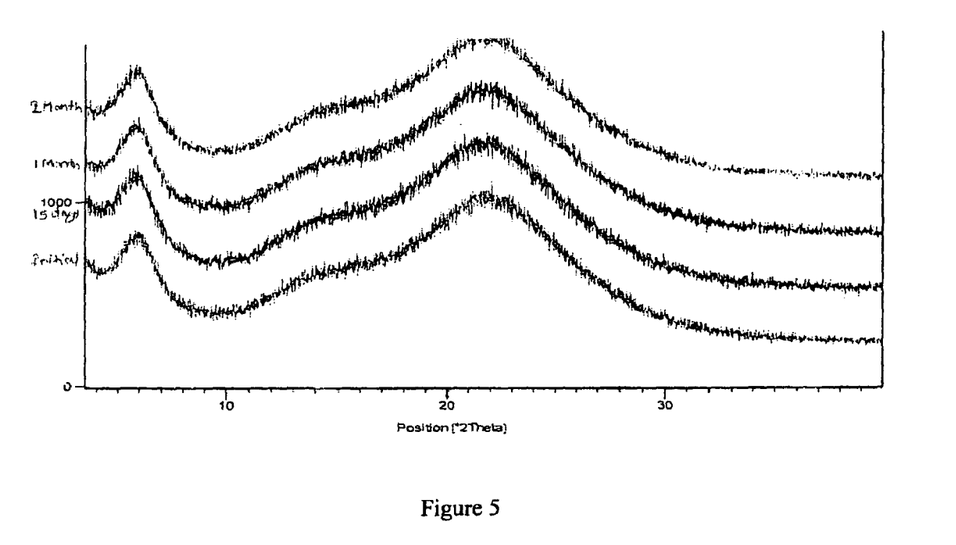
FIG. 5: Stability of stable amorphous form of carvedilol dihydrogen phosphate obtained by using 5% PVPK-30 as stabiliser at 15 days, 1 month and 2 month at 40° C.±2° C. (RH 75%).

The PXRD of stable amorphous form of carvedilol dihydrogen phosphate obtained with stabiliser 5% PVPK-30 after 15 days, 1 month and 2 month at 40° C.±2° C. (RH 75%) is shown in FIG. 5. It does not show sharp peaks that can arise from crystalline form, thus indicating that the amorphous form of carvedilol dihydrogen phosphate obtained with stabiliser is highly stable and does not undergo conversion in to crystalline form.

Thus, it has been unexpectedly found that the stable amorphous form of carvedilol dihydrogen phosphate can be obtained in a simple and reproducible manner. Therefore, the most preferred embodiment of the present invention is to provide highly stable novel amorphous form of carvedilol dihydrogen phosphate.

In an another preferred embodiment, the present invention provide a process for the preparation of stable amorphous form of carvedilol dihydrogen phosphate comprises of:
(a) preparation of a solution of carvedilol base in a suitable solvent or mixture of solvents,
(b) addition of stabiliser,
(c) addition of ortho phosphoric acid,
(d) removal of solvent, and
(e) isolation of solid.

Generally, the aqueous or ortho phosphoric acid is added to the solution of carvedilol base in a suitable solvent. The addition may be performed at a temperature 0-50° C., preferably at 25-30° C. The quantity of carvedilol base and ortho phosphoric acid may be molar equivalent or ortho phosphoric acid may be in slight molar excess.

The present invention further provides another process for the preparation of stable amorphous form of carvedilol dihydrogen phosphate comprises of:
(a) preparation of a solution of polymorph hydrate of carvedilol dihydrogen phosphate in a suitable solvent or mixture of solvents,
(b) addition of stabiliser,
(c) removal of solvent, and
(d) isolation of solid.

The term "suitable solvent" in either of the processes described above includes any protic or aprotic polar solvent or mixture of solvents in which carvedilol is soluble, for example, lower alkanol, dihydroxy solvents, lower aliphatic ketone, and water miscible cyclic and acyclic ethers, cyclic and acyclic amides and nitriles.

The examples of lower alkanol include methanol, ethanol, n-propanol and isopropanol. Dihydroxy solvent such as ethylene glycol and diethylene glycol can also be used. The examples of aliphatic ketone include those acetone, 2-butanone and 4-methyl pentanone. The examples of cyclic ethers include tetrahydrofuran and 1,4-dioxane. The examples of cyclic and acyclic amides include formamide, acetamide, propanamide and 2-methyl pyrrolidinone. The examples of nitrile solvents include acetonitrile and propionitrile. Other polar aptotic solvents like diethylene glycol dimethyl ether, dimethyl sulfoxide, sulfolane can also be useful solvents. The process may also be carried out by using one or two solvents. The preferred suitable solvent is lower alkanol such as methanol, ethanol, propanol and isopropanol and the most preferred solvent is methanol or ethanol.

In either of the process variety of the compounds can be used as stabiliser such as polyvinyl pyrrolidone K-30 (PVPK K-30); 5% Eudragit RSPO, 5% Klucef EXF, 5% Polyethylene glycol-6000 (5% PEG-6000), 5% Polyethylene glycol-4000 (5% PEG-4000), 5% Ethyl cellulose, 5% Hydroxypropyl methyl cellulose (HPFC E-5) and the like.

The quantity of stabiliser can be used in the range 0.01 to 0.1 weight by weight, most preferably 0.05 times weight by weight with respect to carvedilol base or amorphous/crystalline carvedilol dihydrogen phosphate. Stabiliser can added to the solution at temperature 0-250° C., preferably at 50-75° C., most preferably at 50-55° C.

The removal of the solvent before isolation of solid in either of the processes described above is accomplished by techniques which include distillation at atmospheric pressure, distillation under reduced pressure, evaporation, spray drying, freeze drying and agitation thin film evaporation. Moreover, the product obtained may be further dried to achieve the desired moisture values or desired residual solvent values because of the higher glass transition temperature which is in the range of 70-176° C., preferably is in the range of 80-90° C.

The thermodynamically stable forms are always preferred for the formulation because of their advantages. Due to high thermodynamic stability the stable amorphous form of carvedilol dihydrogen phosphate of the present invention is useful for pharmaceutical formulation. The effective amount of stable amorphous form of carvedilol dihydrogen phosphate can be used to prepare pharmaceutical composition in association with one or more non toxic pharmaceutically acceptable carriers and/or diluents thereof, and if desired, other active ingredients, which may be administered orally, intravascularly, intraperitoneally, subcutaneously, intramuscularly or topically for the treatment of hypertension, congestive heart failure and angina in a mammal in need thereof.

The present invention is illustrated by the following representative examples and are not intended to limit the scope of the invention.

EXAMPLES

The powder X-ray diffraction spectrum is measured using Philips (PAN alytical X' pert pro) diffractogram (copper anti cathode) and expressed in terms of inter planar distance d, Bragg's angle 2 theta, intensity and relative intensity (expressed as a percentage of the most intense peak). The scanning parameters included: measurement range: 3-40 degrees two theta; continuous scan.

The FTIR spectra were obtained using a Perkin-Elmer, Spectrum-100 instrument.

The thermogravimetric analysis (TGA) was done using Perkin Elmer Pyris 1 TGA instrument.

Preparation of Stable Amorphous Carvedilol Dihydrogen Phosphate with Stabiliser

Example 1

Preparation of Stable Amorphous Carvedilol Dihydrogen Phosphate Using 5% PVPK-30 as Stabiliser Mixture of 100 g of carvedilol base and 2000 ml methanol was heated at 50-55° C. to get clear solution. To the solution, 27.4 g of 88% ortho phosphoric acid was added dropwise. To the solution, 5 g of PVPK-30 was added. The solvent was distilled off under reduced pressure. Residual solid was scratched to get 120 g of free flowing stable amorphous solid.

Example 2

Preparation of Stable Amorphous Carvedilol Dihydrogen Phosphate Using 5% Eudragit RSPO as Stabiliser Mixture of 10 g of carvedilol base and 200 ml methanol was heated at 50-55° C. to get clear solution. To the solution, 2.74 g of 88% ortho phosphoric acid was added dropwise. To the solution, 0.5 g of 5% Eudragit RSPO was added. The solvent was distilled off under reduced pressure. Residual solid was scratched to get 119 g of free flowing stable amorphous solid.

Example 3

Preparation of Stable Amorphous Carvedilol Dihydrogen Phosphate Using 5% Klucef EXF as Stabiliser Mixture of 10 g of carvedilol base and 200 ml methanol was heated at 50-55° C. to get clear solution. To the solution, 2.74 g of 88% ortho phosphoric acid was added dropwise. To the solution, 0.5 g of 5% Klucef EXF was added. The solvent was distilled off under reduced pressure. Residual solid was scratched to get 122 g of free flowing stable amorphous solid.

Example 4

Preparation of Stable Amorphous Carvedilol Dihydrogen Phosphate Using 5% PEG-6000 as Stabiliser Mixture of 10 g of carvedilol base and 200 ml methanol was heated at 50-55° C. to get clear solution. To the solution, 2.74 g of 88% ortho phosphoric acid was added dropwise. To the solution, 0.5 g of 5% PEG-6000 was added. The solvent was distilled off under reduced pressure. Residual solid was scratched to get 117 g of free flowing stable amorphous solid.

Example 5

Preparation of Stable Amorphous Carvedilol Dihydrogen Phosphate Using 5% Ethyl Cellulose as Stabiliser Mixture of 10 g of carvedilol base and 200 ml methanol was heated at 50-55° C. to get clear solution. To the solution, 2.74 g of 88% ortho phosphoric acid was added dropwise. To the solution, 0.5 g of 5% ethyl cellulose was added. The solvent was distilled off under reduced pressure. Residual solid was scratched to get 120 g of free flowing stable amorphous solid.

Example 6

Preparation of Stable Amorphous Carvedilol Dihydrogen Phosphate Using 5% PEG-4000 as Stabiliser Mixture of 10 g of carvedilol base and 200 ml methanol was heated at 50-55° C. to get clear solution. To the solution, 2.74 g of 88% ortho phosphoric acid was added dropwise. To the solution, 0.5 g of 5% PEG-4000 was added. The solvent was distilled off under reduced pressure. Residual solid was scratched to get 121 g of free flowing stable amorphous solid.

Example 7

Preparation of Stable Amorphous Carvedilol Dihydrogen Phosphate Using 5% HPMC E-5 as Stabiliser Mixture of 10 g of carvedilol base and 200 ml methanol was heated at 50-55° C. to get clear solution. To the solution, 2.74 g of 88% ortho phosphoric acid was added dropwise. To the solution, 0.5 g of 5% HPMC E-5 was added. The solvent was distilled off under reduced pressure. Residual solid was scratched to get 118 g of free flowing stable amorphous solid.

Example 8

Preparation of Amorphous Carvedilol Dihydrogen Phosphate Using Spray Dryer

Carvedilol base (10 g) was dissolved in methanol (500 mL). To the solution, ortho phosphoric acid (2.9 g, 88% aqueous solution,) was added. The solution was subjected to spray drying to afford 5 g of amorphous carvedilol dihydrogen phosphate melting at 62-63° C. having 4.1% moisture content.

Example 9

Preparation of Amorphous Carvedilol Dihydrogen Phosphate

Crystalline carvedilol dihydrogen phosphate (10 g) was dissolved in methanol (750 ml). To the solution, 0.5 g of 5% PVPK-30 was added and the resulting was spray dried to afford 4.7 g of amorphous carvedilol dihydrogen phosphate.

Example 10

Preparation of Stable Amorphous Carvedilol Dihydrogen Phosphate 5% PVPK-30 as Stabiliser

Mixture of 10 g of amorphous carvedilol dihydrogen phosphate obtained in example 8 and 200 ml methanol was heated at 50-55° C. to get clear solution. To the solution, 2.74 g of 88% ortho phosphoric acid was added dropwise. To the solution, 0.5 g of 5% PVPK-30 was added. The solvent was distilled off under reduced pressure. Residual solid was scratched to get 9.2 g of free flowing stable amorphous solid.

Example 11

Preparation of Stable Amorphous Carvedilol Dihydrogen Phosphate Using 5% PVPK-30 as Stabiliser

Mixture of 10 g of crystalline carvedilol dihydrogen phosphate hemihydrate and 200 ml methanol was heated at 50-55° C. to get clear solution. To the solution, 2.74 g of 88% ortho phosphoric acid was added dropwise. To the solution, 0.5 g of 5% PVPK-30 was added. The solvent was distilled off under reduced pressure. Residual solid was scratched to get 9.1 g of free flowing stable amorphous solid.

The invention claimed is:

1. A process for the preparation of stable amorphous form of carvedilol dihydrogen phosphate comprising:
   (a) preparation of a solution of a carvedilol base and phosphoric acid or carvedilol dihydrogen phosphate in a suitable solvent or mixture of solvents,
   (b) addition of stabiliser,
   (c) removal of solvent, and
   (d) isolation of solid.

2. A process according to claim 1 wherein phosphoric acid is added to the solution of carvedilol base in a suitable solvent at a temperature 0-50° C., preferably at 25-30° C.

3. A process according to claim 1 wherein the quantity of carvedilol base and phosphoric acid may be molar equivalent or ortho phosphoric acid may be in slight molar excess.

4. A process according to claim 1 wherein suitable solvent includes any protic or aprotic polar solvent or mixture of solvents selected from lower alkanols, lower aliphatic ketones, water miscible cyclic or acyclic ethers, cyclic or acyclic amides aliphatic nitriles, dimethyl sulfoxide, sulfolane, and mixtures thereof.

5. A process according to claim 4 wherein the solvent is methanol.

6. A process according to claim 1 wherein the stabiliser is selected from a group of polyvinyl pyrrolidone K-30 (PVPK K-30); 5% Eudragit RSPO, 5% Klucef EXF, 5% Polyethylene glycol-6000(5% PEG-6000), 5% Polyethylene glycol-4000 (5% PEG-4000), 5% Ethyl cellulose, 5% Hydroxypropyl methyl cellulose (HPFC E-5).

7. A process according to claim 1 wherein the quantity of stabiliser with respect to the quantity of carvedilol base or amorphous/crystalline carvedilol dihydrogen phosphate is in the range 0.01 to 0.1 weight by weight.

8. A process according to claim 1 wherein the stabiliser is added to the solution at temperature in the range 0-250° C.

9. A process according to claim 1 wherein removal of the solvent before isolation of solid is accomplished by distillation at atmospheric pressure, distillation under reduced pressure, evaporation, spray drying, freeze drying, or agitation thin film evaporation.

10. A process according to claim 4 wherein:
    the lower alkanol comprises methanol, ethanol, n-propanol, isopropanol, or a mixture thereof;
    the lower aliphatic ketones comprises acetone, 2-butanone, 4-methyl pentanone, or a mixture thereof;
    the water miscible cyclic or acyclic ether comprises tetrahydrofuran, 1,4-dioxane, diethylene glycol dimethyl ether, or a mixture thereof;
    the cyclic or acyclic amide comprises formamide, acetamide, propanamide, 2-methyl pyrrolidinone, or a mixture thereof; or
    the aliphatic nitrile comprises acetonitrile, propionitrile, or a mixture thereof.

11. A process according to claim 7 wherein the quantity of stabiliser with respect to the quantity of carvedilol base or amorphous/crystalline carvedilol dihydrogen phosphate is 0.05 times weight by weight.

12. A process according to claim 8 wherein the stabiliser is added to the solution at temperature in the range 50-75° C.

13. A process according to claim 8 wherein the stabiliser is added to the solution at temperature in the range 50-55° C.

* * * * *